United States Patent
Helm et al.

(10) Patent No.: US 12,376,629 B2
(45) Date of Patent: Aug. 5, 2025

(54) NURSING SUPPORT APPARATUS

(71) Applicants: Ryan Andrew Helm, Nashville, TN (US); Judy Gayle Batson Helm, Nashville, TN (US)

(72) Inventors: Ryan Andrew Helm, Nashville, TN (US); Judy Gayle Batson Helm, Nashville, TN (US)

(*) Notice: Subject to any disclaimer, the term of this patent is extended or adjusted under 35 U.S.C. 154(b) by 115 days.

(21) Appl. No.: 18/506,411

(22) Filed: Nov. 10, 2023

(65) Prior Publication Data
US 2025/0151820 A1  May 15, 2025

(51) Int. Cl.
*A41D 1/215* (2018.01)
*A61F 5/058* (2006.01)

(52) U.S. Cl.
CPC .......... *A41D 1/215* (2018.01); *A61F 5/05866* (2013.01)

(58) Field of Classification Search
CPC ...... A47G 9/10; A47G 9/1009; A47G 9/1027; A47G 9/1063; A61F 5/05866; A47D 13/083
See application file for complete search history.

(56) References Cited

U.S. PATENT DOCUMENTS

| | | | |
|---|---|---|---|
| 4,731,890 A * | 3/1988 | Roberts | A47G 9/10 5/636 |
| 5,205,812 A * | 4/1993 | Wasserman | A61F 5/05866 602/5 |
| 5,239,717 A * | 8/1993 | Sue | A47D 13/00 2/104 |
| 6,041,458 A * | 3/2000 | Vickers | A47G 9/10 5/636 |
| 6,328,706 B1 * | 12/2001 | Yattavong | A61F 5/05866 128/878 |
| 6,381,786 B1 * | 5/2002 | Cadden | A47D 13/083 5/655 |
| 7,131,156 B1 * | 11/2006 | Walker-Craft | A47G 9/1045 5/639 |
| 9,226,605 B1 * | 1/2016 | Castellano | A47G 9/0253 |
| 10,729,257 B1 * | 8/2020 | Leach | A47D 13/083 |
| 11,013,347 B1 * | 5/2021 | Sawick | A47D 15/00 |
| 2004/0176714 A1 * | 9/2004 | Darcey | A61F 5/0118 602/21 |
| 2005/0044633 A1 * | 3/2005 | Auxila | A47D 13/083 5/655 |

(Continued)

*Primary Examiner* — David E Sosnowski
(74) *Attorney, Agent, or Firm* — My Patent Guys; Christopher Pilling; Colton Bangs

(57) ABSTRACT

The present invention relates to an ambidextrous nursing support apparatus for preventing wrist strain in caregivers while providing infant comfort. This all-in-one, ergonomic sleeve features an integrated wrist guard and a cushioned portion, extending from the caregiver's elbow to the palm. The wrist guard ensures the caregiver's wrist remains in a neutral position, reducing the risk of repetitive strain injuries such as De Quervain's tenosynovitis. The cushion offers a soft platform for supporting the infant's body and head. Two openings in the sleeve allow for either thumb to exit the sleeve, as well as an opening for the caregiver's fingers, enhancing mobility and functionality. This compact, unified design simplifies caregiving tasks, combining comfort and support for both the caregiver and infant.

14 Claims, 3 Drawing Sheets

(56) References Cited

U.S. PATENT DOCUMENTS

| | | | | |
|---|---|---|---|---|
| 2005/0273030 | A1* | 12/2005 | Koby | A61F 5/0118 |
| | | | | 602/21 |
| 2006/0179574 | A1* | 8/2006 | Margalit | A47D 13/02 |
| | | | | 5/655 |
| 2008/0028530 | A1* | 2/2008 | Hao | A47G 9/10 |
| | | | | 5/636 |
| 2008/0141462 | A1* | 6/2008 | Woods | A47C 20/023 |
| | | | | 5/655 |
| 2008/0306419 | A1* | 12/2008 | Bishop | A61G 7/05738 |
| | | | | 5/625 |
| 2008/0313813 | A1* | 12/2008 | Adiri | A47D 13/083 |
| | | | | 5/655 |
| 2010/0043147 | A1* | 2/2010 | Popp | A47G 9/10 |
| | | | | 5/636 |
| 2012/0260430 | A1* | 10/2012 | Hernandez | A47D 13/083 |
| | | | | 5/655 |
| 2015/0101125 | A1* | 4/2015 | Fang | A47D 13/08 |
| | | | | 5/655 |
| 2016/0235216 | A1* | 8/2016 | Einhorn | A47D 13/083 |
| 2020/0237121 | A1* | 7/2020 | Brooks | A47G 9/10 |
| 2023/0380608 | A1* | 11/2023 | Pesale | A47C 7/425 |
| 2024/0299741 | A1* | 9/2024 | Finkelstein | A61N 1/36034 |
| 2024/0341509 | A1* | 10/2024 | Rubin | A41D 20/00 |
| 2024/0389772 | A1* | 11/2024 | Nassar | A47G 9/1081 |
| 2025/0127313 | A1* | 4/2025 | Sauceda | A61F 7/02 |

* cited by examiner

NURSING SUPPORT APPARATUS

CROSS-REFERENCE TO RELATED APPLICATIONS

N/A

BACKGROUND OF THE INVENTION

1. Field of the Invention

The present invention relates generally to infant care devices but more particularly to a nursing support apparatus.

2. Description of Related Art

Caring for infants or babies often involves prolonged periods where the caregiver, such as a mother or other attendant, must hold or nurse the infant. During these periods, the caregiver's arms and especially the wrists are subjected to continuous strain due to the weight of the infant and the necessity of maintaining a secure yet comfortable position for both the caregiver and the infant. Prolonged stress on the wrists, in particular, can lead to a variety of musculoskeletal issues, one of the most common being "mommy wrist" or De Quervain's tenosynovitis. This condition is characterized by pain and inflammation of the tendons on the thumb side of the wrist and can severely impede a caregiver's ability to comfortably and effectively hold or nurse their infant.

Existing solutions, such as nursing pillows and cushions are focused on providing support for the infant and do not address the ergonomic needs of the caregiver's wrist and arm. While these products do alleviate some strain by supporting the infant's weight, none offer a dedicated means to maintain the caregiver's wrist in an ergonomically correct position to prevent the onset of musculoskeletal issues.

Consequently, there remains a need for a device that can provide comfortable support for the infant while simultaneously protecting the caregiver's wrist against strains and injuries commonly associated with nursing and holding an infant for extended periods.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

It is a particular object of the present invention to provide a nursing support apparatus that minimizes the risk of "mommy wrist" or De Quervain's tenosynovitis among caregivers by maintaining the wrist in an ergonomic position during the act of nursing or cradling an infant. It is another object of the present invention to provide a nursing support apparatus that includes a cushion portion to support an infant's body and head comfortably. It is yet another object of the present invention to provide an apparatus that is ambidextrous in design, allowing caregivers to wear the apparatus on either arm with equal comfort and support functionality. Finally, it is another object of the present invention to provide a nursing support apparatus that equally distributes the weight of an infant across the caregiver's forearm, thereby reducing localized pressure and strain on the wrist and arm.

In order to do so, a nursing support apparatus is provided, comprising an elongated sleeve configured to be worn on a caregiver's forearm; an integrated wrist guard within the sleeve for maintaining the caregiver's wrist in an ergonomic position; and a cushion portion surrounding the sleeve to support the infant's head and body.

In one embodiment, the elongated sleeve is ambidextrous and capable of being worn on either the left or right arm of the caregiver. In another embodiment, the integrated wrist guard comprises a splint to prevent flexion of the caregiver's wrist. In one embodiment, the cushion portion is wider than the caregiver's forearm and wrist to provide lateral support for the infant. In yet another embodiment, at least one thumb cutout located on the sleeve is provided to allow the caregiver's thumb to protrude from the sleeve. In one embodiment, the sleeve terminates near the wearer's palm, allowing the caregiver's fingers to remain free and functional for additional tasks. In another embodiment, the cushion portion comprises a soft, pillow-type material.

In another aspect of the invention, a nursing support apparatus for preventing wrist injuries in caregivers while providing support to an infant is provided, the apparatus comprising an elongated sleeve configured to be worn on a caregiver's forearm, constructed to distribute the weight of an infant across the caregiver's arm and reduce localized pressure points; an integrated wrist guard within the sleeve, the wrist guard being anatomically shaped to maintain the caregiver's wrist in a neutral, ergonomic position conducive to minimizing the risk of repetitive strain injuries; and, a cushion portion enveloping the sleeve and extending beyond the caregiver's forearm perimeter.

The foregoing has outlined rather broadly the more pertinent and important features of the present invention so that the detailed description of the invention that follows may be better understood and so that the present contribution to the art can be more fully appreciated. Additional features of the invention, which will be described hereinafter, form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF THE DRAWINGS

Other features and advantages of the present invention will become apparent when the following detailed description is read in conjunction with the accompanying drawings, in which.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein to specifically provide a support system for a nursing support apparatus.

It is to be understood that the terminology used herein is for the purpose of describing particular embodiments only and is not intended to be limiting. The terms "a" or "an," as used herein, are defined to mean "at least one." The term "plurality," as used herein, is defined as two or more. The term "another," as used herein, is defined as at least a second or more. The terms "including" and/or "having," as used herein, are defined as comprising (i.e., open language). The term "providing" is defined herein in its broadest sense, e.g., bringing/coming into physical existence, making available, and/or supplying to someone or something, in whole or in multiple parts at once or over a period of time. These terms generally refer to a range of numbers that one of skill in the art would consider equivalent to the recited values (i.e., having the same function or result). In many instances these terms may include numbers that are rounded to the nearest significant figure.

Figure 1:
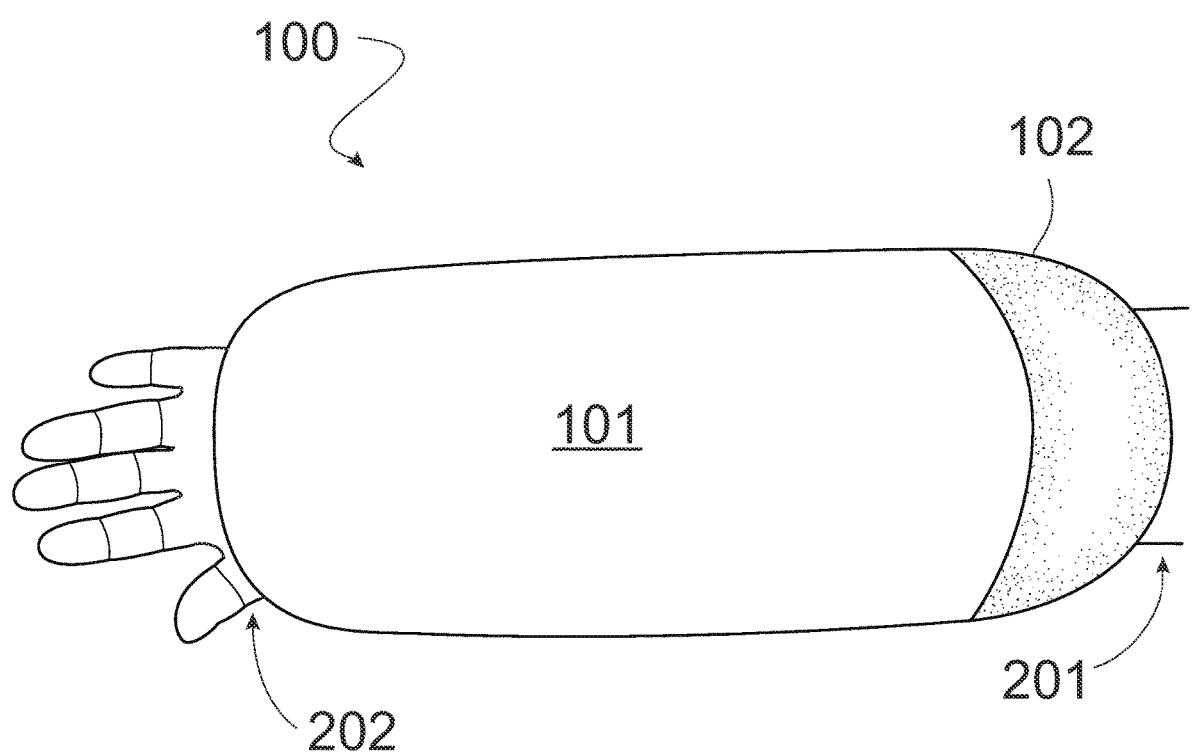
FIG. 1 is a perspective view of the nursing support apparatus on a wearer's arm according to an embodiment of the present invention.
Figure 2:
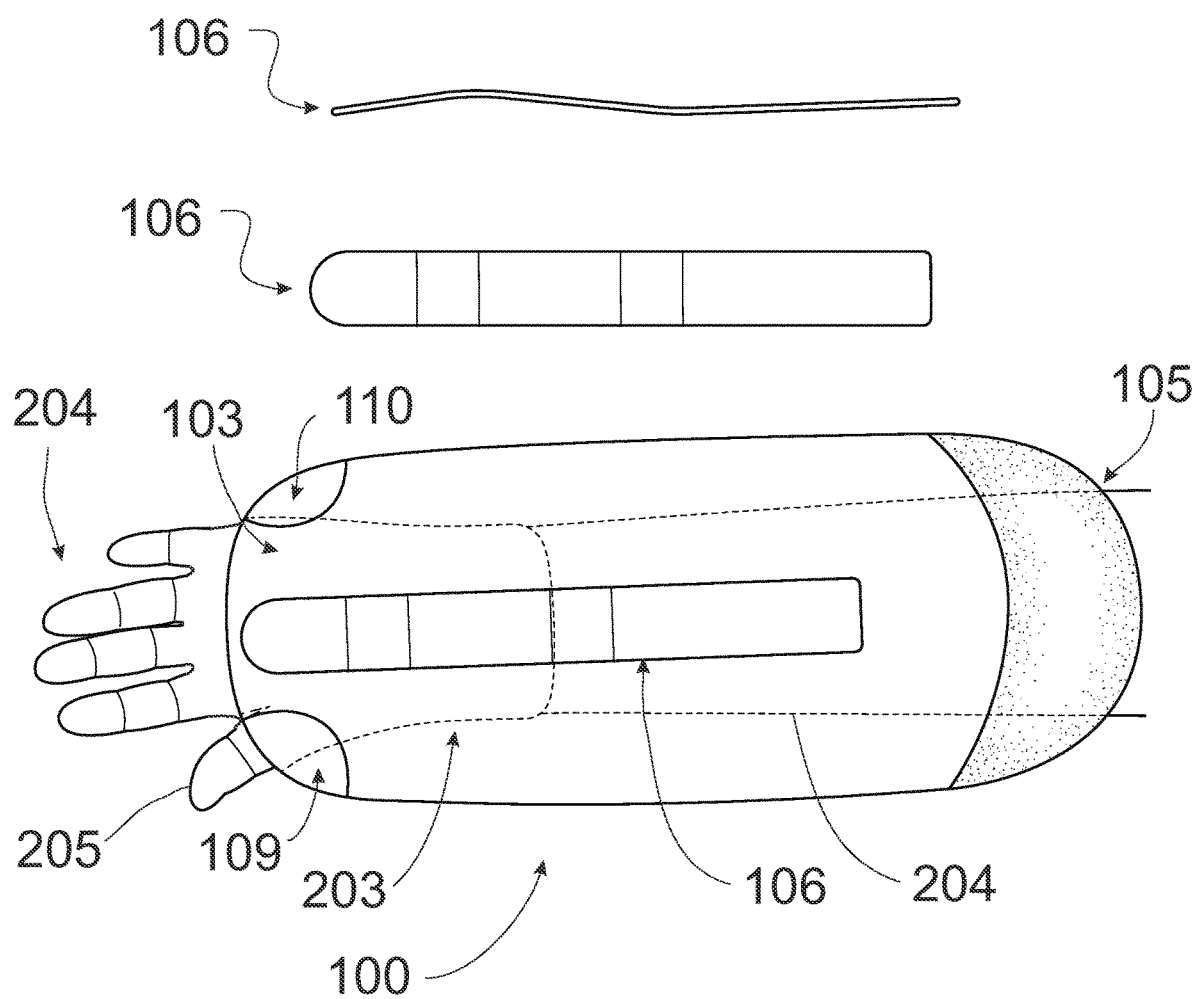
FIG. 2 is a transparent view of FIG. 1 showing the inner sleeve the apparatus and wrist support element according to an embodiment of the present invention.
Figure 3:
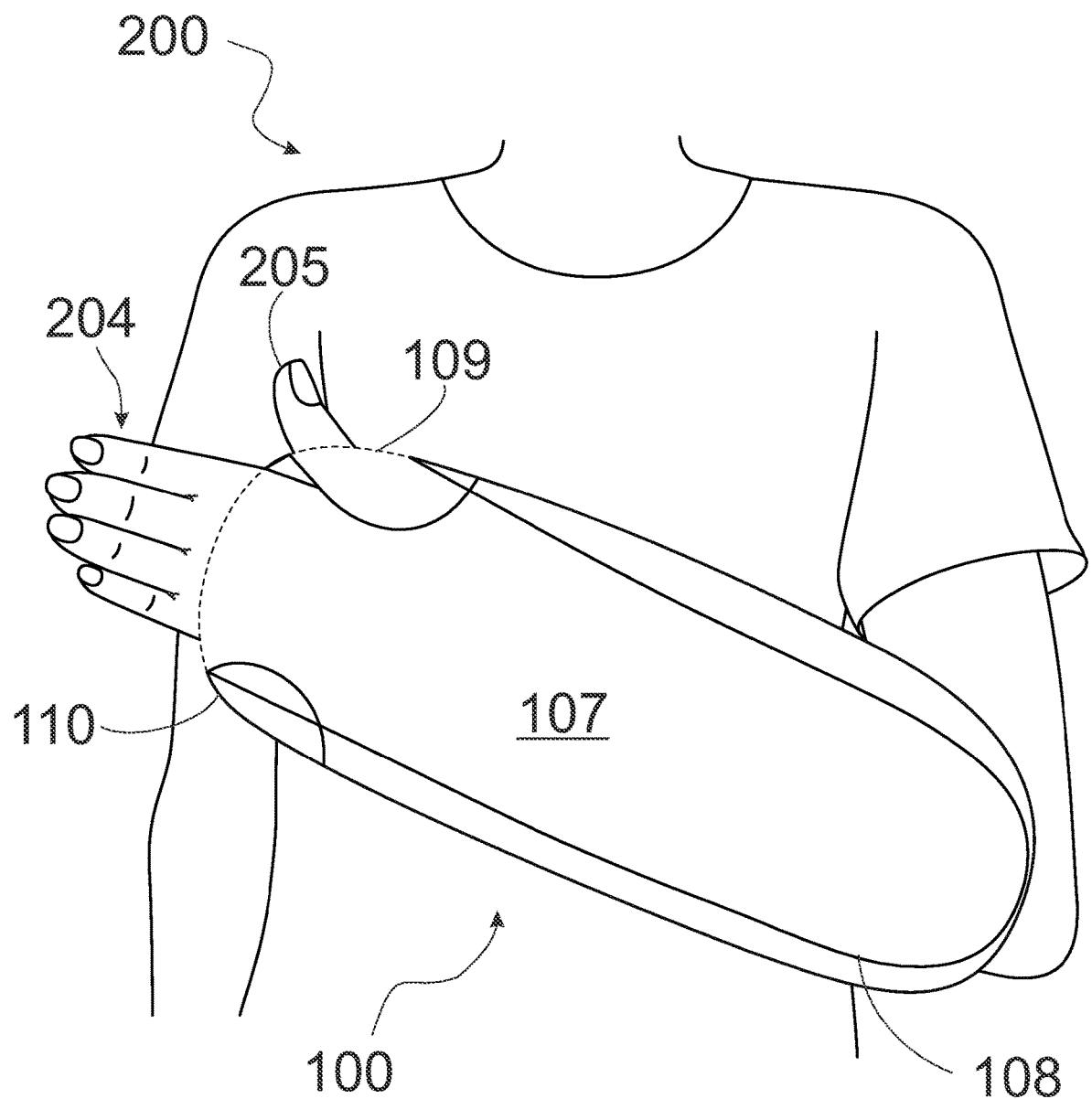
FIG. 3 is a perspective view of the back side of the nursing support apparatus on a wearer's arm according to an embodiment of the present invention.

Referring to any of the accompanying FIGS. 1-3, a nursing support apparatus 100 is illustrated. The apparatus 100 is designed to provide ergonomic support for a caregiver's arm and wrist and comfort for an infant during nursing or holding. The apparatus 100 comprises a support surface 101 that defines a cushion portion to support an infant's body and head comfortably. In some embodiments, the cushion portion includes a headrest 102 at its distal end to further support an infant's head during use. It should be noted that the headrest is an optional feature.

The apparatus 100 is advantageously configured to be worn over the arm 201 of the wearer 200, who may be a nursing mother or another caregiver. The apparatus 100 is designed to extend from the inside of the wearer's elbow to approximately the palm 202 of the wearer's hand, providing substantial coverage and support. However, it should be understood that the length of the apparatus may vary.

An opening 105 is provided to allow the wearer to insert their hand and arm into the apparatus 100, accessing an inner sleeve 108. The sleeve 108 is configured to snugly fit over the wearer's forearm 204 and wrist 203, providing comfortable yet secure support.

In one embodiment, a wrist guard 103 is seamlessly integrated within the sleeve 108. The wrist guard 103, which in some embodiments, includes a wrist splint 106, is strategically placed to maintain the wearer's wrist in an ergonomically advantageous position, mitigating the risk of injuries such as those caused by repetitive strain or improper positioning while holding or nursing an infant. In some embodiments, the wrist guard 103 is constructed from semi-rigid material.

Further details of the wrist splint 106 are shown in FIG. 2, where side and top views show the structure and shape of wrist splint. The wrist splint is specifically designed to prevent bending of the wearer's wrist towards the palm, a common cause of strain on the wrist tendons, particularly when a caregiver supports an infant's head in a cradle position during feeding.

In order to accommodate use on either arm, the apparatus 100 is designed to be ambidextrous. To this end, two thumb cutouts 109 and 110 are provided to enable the thumb 205 of the user to protrude from the sleeve when in use, thus allowing for greater mobility and functionality of the hand.

The termination of the sleeve near the wearer's palm ensures that the wearer's fingers 204 remain free and unobstructed, allowing for additional tasks to be performed without the need to remove the apparatus. As shown in the figures, the apparatus is fitted to a left hand/forearm; however, due to its ambidextrous design, it can be easily adapted for use on the right arm with equal efficacy.

The cushion portion 101 of the apparatus is constructed of a soft, pillow-type material. This material is chosen for its gentle yet supportive properties, providing a comfortable resting surface for the infant. In some embodiments, the cushion portion is configured to be wider than the wearer's arm, forearm, and wrist, ensuring that it not only supports but also cradles the infant during use. In some embodiments, the cushion portion comprises hypoallergenic materials, including but not limited to cotton, microfiber, polyester, silk, rayon, or similar materials. In some embodiments, the rear or back side 107 of the apparatus 100 may include pillow or cushion material. In alternative embodiments, the cushion portion is only provided on the front side of the apparatus as shown in FIG. 1.

Advantageously, the nursing support apparatus 100 provides a significant improvement over existing nursing aids by combining the dual functionality of ergonomic support and infant comfort into a single, easy-to-use device. The apparatus offers a solution to the common physical discomforts experienced by caregivers during nursing and holding, fostering a more nurturing and pain-free bonding experience.

The nursing support apparatus 100 is configured as an all-in-one unit, with the inner sleeve 108, wrist guard 103, and cushion portion 101 forming a cohesive and integrated assembly. This integration is essential for ensuring consistent positioning and stability of the apparatus during use. The singular unit construction eliminates the need for separate components, which can be cumbersome and may require frequent adjustments. By combining the wrist guard and cushion into a single entity, the apparatus not only simplifies the caregiver's experience but also enhances the overall functionality of the device. The unibody design further ensures that the cushion portion remains in optimal alignment with the wearer's arm and the infant's body, providing continuous support without shifting or bunching. Thus the present invention provides ease of use, superior comfort, and effective support, thereby addressing the common challenges faced by caregivers during nursing and infant care.

The nursing support apparatus is configured to accommodate a wide range of caregiver body types. To this end, the apparatus may be implemented as a one-size-fits-all solution, leveraging adjustable components such as stretchable fabrics, Velcro® straps, or elasticated elements that enable a snug fit across various wrist and forearm sizes. This universal design approach simplifies the manufacturing process and reduces the complexity of inventory management. Alternatively, to cater to the diverse anatomical requirements of potential users, the apparatus could be offered in multiple sizes. Each size variant may be calibrated to ensure an optimal fit for different wrist and forearm dimensions, thereby maximizing comfort and ergonomic benefit for the caregiver. Size options may be provided in small/medium and large/extra-large categories or could be based on actual measurements of forearm circumference and wrist diameter to provide a more tailored fit. This size range ensures that the apparatus can accommodate individual variations in caregiver physiques, providing inclusive and accessible support for all who need it. It should be noted that the sizing or adjustment of sizing is outside the scope or inventive nature of the invention.

Although the invention has been described in considerable detail in language specific to structural features, it is to be understood that the invention defined in the appended claims is not necessarily limited to the specific features described. Rather, the specific features are disclosed as exemplary forms of implementing the claimed invention. The terminology and phraseology used in this description and the abstract are for illustrative purposes and should not be considered as limiting. Therefore, while exemplary illustrative embodiments of the invention have been described, numerous variations and alternative embodiments will occur to those skilled in the art. Such variations and alternative embodiments are contemplated, and can be made without departing from the spirit and scope of the invention.

It should further be noted that throughout the entire disclosure, the labels such as left, right, front, back, top, bottom, forward, reverse, clockwise, counterclockwise, up, down, or other similar terms such as upper, lower, aft, fore, vertical, horizontal, oblique, proximal, distal, parallel, perpendicular, transverse, longitudinal, etc. have been used for convenience purposes only and are not intended to imply any particular fixed direction or orientation. Instead, they are used to reflect relative locations and/or directions/orientations between various portions of an object.

In addition, references to "first," "second," "third," and so fourth members throughout the disclosure (and in particular, claims) are not used to show a serial or numerical limitation but instead are used to distinguish or identify the various members of the group.

What is claimed is:

1. A nursing support apparatus configured to be worn on a caregiver's arm, comprising:
    an elongated sleeve configured to be worn on a caregiver's forearm;
    an integrated wrist guard comprising a splint to prevent flexion of a caregiver's wrist, the integrated wrist guard comprised of a material within the sleeve for maintaining the caregiver's wrist in an ergonomic position; and,
    a cushion portion surrounding the sleeve to comfortably support an infant's head and body.

2. The nursing support apparatus of claim 1, wherein the elongated sleeve is ambidextrous and capable of being worn on either a left forearm or a right forearm of the caregiver.

3. The nursing support apparatus of claim 2, further comprising two thumb cutouts on the sleeve, one being configured to allow a left thumb of the caregiver to protrude from the sleeve and the other one of the two thumb cutouts configured to allow a right thumb of the caregiver to protrude from the sleeve.

4. The nursing support apparatus of claim 1, wherein the cushion portion is configured to be wider than the caregiver's forearm and wrist to provide lateral support for the infant.

5. The nursing support apparatus of claim 1, wherein the sleeve is configured to terminate at a palm of the caregiver, allowing one or more fingers of the caregiver to remain free and functional for additional tasks.

6. The nursing support apparatus of claim 1, wherein the cushion portion comprises a hypoallergenic material.

7. A nursing support apparatus configured to be worn on a caregiver's arm for preventing wrist injuries in caregivers while providing support to an infant, the apparatus comprising:
    an elongated sleeve configured to be worn on a caregiver's forearm, constructed to distribute the weight of an infant across the caregiver's arm and reduce localized pressure points;
    an integrated wrist guard comprising a splint to prevent flexion of a caregiver's wrist, the integrated wrist guard comprised of a material within the sleeve, the wrist guard being anatomically shaped to maintain the caregiver's wrist in a neutral, ergonomic position conducive to minimizing the risk of repetitive strain injuries; and,
    a cushion portion enveloping the sleeve.

8. The nursing support apparatus of claim 7, wherein the elongated sleeve is ambidextrous and capable of being worn on either a left forearm or a right forearm of the caregiver.

9. The nursing support apparatus of claim 7, wherein the cushion portion is configured to be wider than the caregiver's forearm and wrist to provide lateral support for the infant.

10. The nursing support apparatus of claim 7, wherein the sleeve is configured to terminate at a palm of the caregiver, allowing one or more fingers of the caregiver to remain free and functional for additional tasks.

11. The nursing support apparatus of claim 7, wherein the cushion portion comprises a hypoallergenic material.

12. The nursing support apparatus of claim 7, wherein the cushion portion includes a contoured headrest configured to support an infant's head and promote a proper feeding posture for the infant.

13. The nursing support apparatus of claim 7, wherein the elongated sleeve is ambidextrous and capable of being worn on either a left forearm or a right forearm of the caregiver.

14. The nursing support apparatus of claim 13, further comprising two thumb cutouts on the sleeve, one being configured to allow a left thumb of the caregiver to protrude from the sleeve and the other one of the two thumb cutouts configured to allow a right thumb of the caregiver to protrude from the sleeve.

* * * * *